United States Patent [19]

Lau et al.

[11] Patent Number: 4,585,898

[45] Date of Patent: Apr. 29, 1986

[54] PREPARATION OF SUBSTITUTED BENZALDEHYDES

[75] Inventors: Roland L. Lau; John S. Hudson, both of Columbia, S.C.

[73] Assignee: Hardwicke Chemical Company, Elgin, S.C.

[21] Appl. No.: 683,027

[22] Filed: Dec. 18, 1984

[51] Int. Cl.$^4$ ............................................. C07C 45/63
[52] U.S. Cl. ..................................................... 568/433
[58] Field of Search ......................................... 568/433

[56] References Cited

U.S. PATENT DOCUMENTS 4,036,887  7/1977  Sheldon et al. ..................... 568/433

FOREIGN PATENT DOCUMENTS 0077021  6/1977  Japan .................................. 568/433

Primary Examiner—Bernard Helfin
Attorney, Agent, or Firm—Donald L. Johnson; John F. Sieberth; Patricia J. Hogan

[57] ABSTRACT

3-Bromobenzaldehydes are prepared by reacting a benzaldehyde having a free 3-position with bromine chloride in the presence of aluminum chloride and a small amount of dibromomethane.

9 Claims, No Drawings

PREPARATION OF SUBSTITUTED BENZALDEHYDES

FIELD OF INVENTION

This invention relates to 3-bromobenzaldehydes and more particularly to a process for preparing them.

BACKGROUND

As disclosed in U.S. Pat. No. 4,036,887 (Sheldon et al.), 3-bromobenzaldehyde is useful as an insecticide precursor and can be prepared by reacting benzaldehyde with bromine chloride in the presence of aluminum chloride and about 140-500 ml of a chloroalkane, such as dichloromethane, 1,2-dichloroethane, or chloroform, per mol of benzaldehyde. This process has advantages over other known techniques of synthesizing 3-bromobenzaldehyde, but it also has disadvantages. Specifically, the process of Sheldon et al. leads to the formation of as much as 5% of 3-chloro derivatives, thus reducing the efficiency of the process and making product isolation more difficult. Also, the use of 1,2-dichloroethane, the preferred solvent of Sheldon et al., leads to the formation of 1,2-dibromoethane, a toxic material which is undesirable even in trace quantities and the formation of which complicates product isolation and aqueous waste disposal.

SUMMARY OF INVENTION

An object of this invention is to provide a novel process for preparing 3-bromobenzaldehydes.

Another object is to provide such a process which is efficient and commercially attractive.

A further object is to provide such a process which produces no 1,2-dibromoethane and only negligible amounts of 3-chloro derivatives.

These and other objects are attained by reacting a benzaldehyde with bromine chloride in the presence of aluminum chloride and a small amount of dibromomethane.

DETAILED DESCRIPTION

Benzaldehydes useful in the practice of the invention are benzaldehydes having a free 3-position, the 2-, 4-, and/or 5-positions optionally bearing inert substituents, such as fluoro, chloro, t-butyl, phenyl, phenoxy, etc. The preferred benzaldehydes are benzaldehyde itself and 4-fluorobenzaldehyde.

Except for the nature of the reaction medium and the amount employed, the process of the invention is very similar to the process of Sheldon et al., the teachings of which are incorporated herein by reference. Thus, it is preferred to:

(1) react one molar proportion of benzaldehyde with about 0.9-1.2 molar proportions of bromine chloride in the presence of about 1.1-2.2 molar proportions of aluminum chloride and a small amount of dibromomethane, specifically about 0.3-0.9 mol of dibromomethane per mol of aluminum chloride, (2) employ substantially anhydrous conditions and a temperature which, like the temperature of Sheldon et al., is below 100° C. but, unlike the temperature of Sheldon et al., is preferably in the range of about 40°-95° C., more preferably about 50°-70° C., (3) combine the reactants by gradually adding the bromine chloride to a dibromomethane slurry of the benzaldehyde and aluminum chloride (at least most of which is actually the benzaldehyde/aluminum chloride complex mentioned by Sheldon et al.), (4) remove by-product hydrogen chloride essentially as it is formed, (5) maintain the reaction temperature until the reaction is substantially complete, e.g., throughout the addition of the bromine chloride and for about an hour thereafter, and (6) isolate the product by conventional techniques.

The use of dibromomethane in the specified amounts makes the process an efficient, commercially attractive method of preparing 3-bromobenzaldehydes in high yield and high purity without the formation of 1,2-dibromoethane or more than a negligible amount of 3-chloro derivatives. The achievement of these desirable results is particularly surprising since (1) Sheldon et al. indicate that the reaction medium for such a process should be a solvent for the reactants but (2) dibromomethane is not a medium in which the reactants are mutually soluble.

The following example is given to illustrate the invention and is not intended as a limitation thereof.

EXAMPLE

Charge 0.8 molar proportion of dibromomethane and 1.3 molar proportions of anhydrous aluminum chloride to a suitable reaction vessel. Add one molar proportion of benzaldehyde to the resultant slurry with agitation over a period of one hour at 40°-50° C. After completing the addition of the benzaldehyde, add one molar proportion of bromine chloride over a period of 4-5 hours while continuing agitation and maintaining the pot temperature at 50°-70° C. Continue agitation for an additional hour at 60°-70° C. Transfer the reaction mass to a flask containing dilute hydrochloric acid, separate the organic, and recover the solvent by distillation. The process results in the formation of 3-bromobenzaldehyde which is isolated in an 85% yield (99+% purity) by vacuum distillation.

It is obvious that many variations can be made in the products and processes set forth above without departing from the spirit and scope of this invention.

We claim:

1. In a process for preparing a 3-bromobenzaldehyde by reacting a benzaldehyde having a free 3-position with bromine chloride in the presence of aluminum chloride, the improvement which comprises conducting the reaction in the presence of about 0.3-0.9 mol of dibromomethane per mole of aluminum chloride.

2. The process of claim 1 wherein the benzaldehyde is benzaldehyde.

3. The process of claim 1 wherein the benzaldehyde is 4-fluorobenzaldehyde.

4. The process of claim 1 wherein one molar proportion of the benzaldehyde is reacted with about 0.9-1.2 molar proportions of bromine chloride in the presence of about 1.1-2.2 molar proportions of aluminum chloride at a temperature in the range of about 40°-95° C.

5. The process of claim 4 wherein the temperature is in the range of about 50°-70° C.

6. The process of claim 1 wherein the reaction is conducted under substantially anhydrous conditions.

7. The process of claim 1 wherein the reaction is conducted by gradually adding the bromine chloride to a dibromomethane slurry of the benzaldehyde and aluminum chloride.

8. A process which comprises reacting one molar proportion of benzaldehyde with about 0.9-1.2 molar proportions of bromine chloride in the presence of about 1.1–2.2 molar proportions of aluminum chloride and about 0.3–0.9 mol of dibromomethane per mol of aluminum chloride under substantially anhydrous conditions at a temperature in the range of about 40°–95° C. so as to form 3-bromobenzaldehyde, the components of the reaction mixture being combined by gradually adding the bromine chloride to a dibromomethane slurry of the benzaldehyde and aluminum chloride.

9. The process of claim 8 wherein the temperature is in the range of about 50°–70° C.

* * * * *